(12) United States Patent
Chernyak et al.

(10) Patent No.: US 7,846,152 B2
(45) Date of Patent: Dec. 7, 2010

(54) CALIBRATING LASER BEAM POSITION AND SHAPE USING AN IMAGE CAPTURE DEVICE

(75) Inventors: Dimitri A. Chernyak, Sunnyvale, CA (US); Keith Holliday, San Jose, CA (US); Mathew Clopp, Santa Clara, CA (US)

(73) Assignee: AMO Manufacturing USA, LLC., Milpitas, CA (US)

( * ) Notice: Subject to any disclaimer, the term of this patent is extended or adjusted under 35 U.S.C. 154(b) by 1700 days.

(21) Appl. No.: 10/808,728

(22) Filed: Mar. 24, 2004

(65) Prior Publication Data
US 2005/0215986 A1    Sep. 29, 2005

(51) Int. Cl.
*A61F 9/008* (2006.01)
*G01N 21/00* (2006.01)
*G01B 11/00* (2006.01)

(52) U.S. Cl. .............................. 606/10; 606/5; 356/72; 356/390

(58) Field of Classification Search .................... 606/5, 606/10–13; 396/245; 356/72, 388–390
See application file for complete search history.

(56) References Cited

U.S. PATENT DOCUMENTS

| | | | |
|---|---|---|---|
| 3,364,493 A | 1/1968 | Myer | |
| 3,986,767 A | 10/1976 | Rexer et al. | |
| 4,665,913 A | 5/1987 | L'Esperance, Jr. | |
| 4,669,466 A | 6/1987 | Hirota et al. | |
| 4,732,148 A * | 3/1988 | L'Esperance, Jr. | 606/5 |
| 4,770,172 A | 9/1988 | L'Esperance, Jr. | |
| 4,773,414 A | 9/1988 | L'Esperance, Jr. | |
| 4,980,881 A | 7/1991 | Sheets | |
| 5,078,491 A | 1/1992 | Johnston, Jr. | |
| 5,144,630 A | 9/1992 | Lin | |
| 5,163,934 A | 11/1992 | Munnerlyn | |
| 5,261,822 A | 11/1993 | Hall et al. | |

(Continued)

FOREIGN PATENT DOCUMENTS

CA    2065174 A1    10/1992

(Continued)

OTHER PUBLICATIONS

Borsutzky, A. et al. (1991). "Tunable UV Radiation at Short Wavelengths (188-240 nm) Generated by Sum-Frequency Mixing in Lithium Borate," Appl. Phys. B 52, 380-384.

(Continued)

*Primary Examiner*—David Shay

(57) ABSTRACT

The present invention provides improved methods and systems for laser beam positioning, shape profile, size profile, drift, and/or deflection calibration using an image capture device, such as a microscope camera, for enhanced calibration accuracy and precision. The methods and systems are particularly suited for iris calibration and hysteresis measurement of a variable diameter aperture. One method for calibrating laser pulses from a laser eye surgery system using an image capture device comprises imaging a known object with an image capture device. A pulsed laser beam is directed onto a calibration surface so as to leave a mark on the calibration surface. The mark on the calibration surface is then imaged with the image capture device. The laser eye surgery system is calibrated by comparing the image of the mark on the calibration surface to the image of the known object.

23 Claims, 7 Drawing Sheets

U.S. PATENT DOCUMENTS

| | | | |
|---|---|---|---|
| 5,267,012 | A | 11/1993 | Sasnett et al. |
| 5,365,032 | A | 11/1994 | Müller et al. |
| 5,556,395 | A | 9/1996 | Shimmick et al. |
| 5,620,437 | A | 4/1997 | Sumiya |
| 5,683,379 | A | 11/1997 | Hohla |
| 5,742,626 | A | 4/1998 | Mead et al. |
| 5,772,656 | A | 6/1998 | Klopotek |
| 5,782,822 | A * | 7/1998 | Telfair et al. .................. 606/5 |
| 5,814,042 | A | 9/1998 | Zair |
| 5,825,562 | A | 10/1998 | Lai et al. |
| 5,865,830 | A | 2/1999 | Parel et al. |
| 5,912,775 | A | 6/1999 | Glocker |
| 6,090,102 | A | 7/2000 | Telfair et al. |
| 6,116,737 | A * | 9/2000 | Kern ............................. 606/5 |
| 6,129,722 | A | 10/2000 | Ruiz |
| 6,172,329 | B1 | 1/2001 | Shoemaker et al. |
| 6,195,164 | B1 | 2/2001 | Thompson et al. |
| 6,210,169 | B1 | 4/2001 | Yavitz |
| 6,210,401 | B1 | 4/2001 | Lai |
| 6,320,699 | B1 | 11/2001 | Maeda et al. |
| 6,322,555 | B1 | 11/2001 | LaHaye |
| 6,331,177 | B1 | 12/2001 | Munnerlyn et al. |
| 6,404,457 | B1 * | 6/2002 | Noh .......................... 396/245 |
| 6,559,934 | B1 | 5/2003 | Yee et al. |
| 6,666,855 | B2 | 12/2003 | Yee et al. |
| 6,817,998 | B2 | 11/2004 | LaHaye |
| 2002/0077622 | A1 * | 6/2002 | Hofer .............................. 606/5 |
| 2002/0120198 | A1 | 8/2002 | Nakamura |
| 2004/0042080 | A1 | 3/2004 | Caudle et al. |

FOREIGN PATENT DOCUMENTS

| | | |
|---|---|---|
| WO | WO 94/25836 A1 | 11/1994 |
| WO | WO 99/24796 A1 | 6/1999 |
| WO | WO 01/10322 A1 | 2/2001 |
| WO | WO 02/76319 A1 | 3/2002 |
| WO | WO 03/092565 A1 | 11/2003 |

OTHER PUBLICATIONS

Talk, "Photodiode" Wikipedia, May 14, 2004 (2 pgs total).
Supplementary Partial European Search Report, Application No. 05729130, date of completion of search: Nov. 6, 2009, 2 pages total.

* cited by examiner

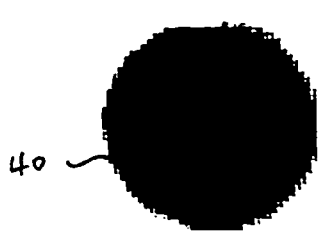
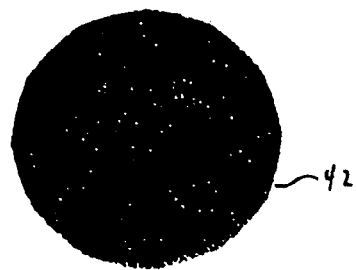
FIG. 4A  FIG. 4B
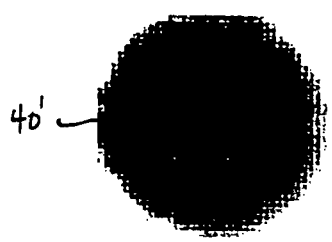
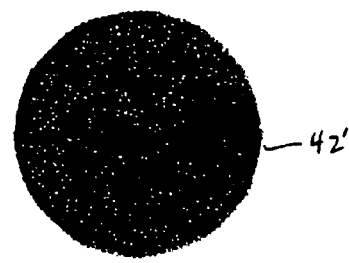
FIG. 5A  FIG. 5B
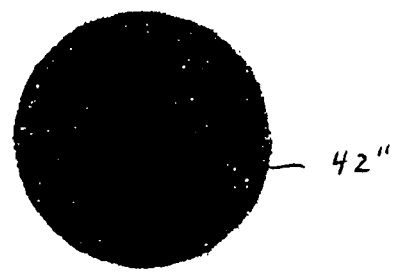
FIG. 6A  FIG. 6B
| Diameter set (mm) | Profilometer (mm) | up/down: best fit (mm) | up/up: best fit (mm) | Difference: u/u – u/d (mm) | Difference: prof – u/d (mm) |
| --- | --- | --- | --- | --- | --- |
| 0.65 | 0.59 | 0.58 | 0.59 | 0.01 | 0.01 |
| 1.00 | 0.89 | 0.85 | 0.85 | 0.00 | 0.04 |
| 2.00 | 1.98 | 1.96 | 1.95 | -0.01 | 0.02 |
| 3.00 | 2.92 | 2.98 | 3.02 | 0.04 | -0.06 |
| 4.00 | 3.98 | 3.98 | 3.95 | -0.03 | 0.00 |
| 5.00 | 4.90 | 4.92 | 4.91 | -0.01 | -0.02 |
| 6.00 | 5.87 | 5.87 | 5.77 | -0.10 | 0.00 |
FIG. 7

CALIBRATING LASER BEAM POSITION AND SHAPE USING AN IMAGE CAPTURE DEVICE

BACKGROUND OF THE INVENTION

1. Field of the Invention

The present invention relates generally to methods and systems for calibrating laser beam delivery systems, particularly ophthalmological surgery systems. More specifically, the present invention relates to methods and systems for calibrating a laser beam, such as a position or shape of the laser beam, from the laser beam delivery system using an image capture device.

Laser based systems are now commonly used in ophthalmological surgery on corneal tissues of the eye to correct vision defects. These systems use lasers to achieve a desired change in corneal shape, with the laser removing microscopic layers of stromal tissue from the cornea using a technique generally described as ablative photodecomposition to alter the refractive characteristics of the eye. Laser eye surgery techniques are useful in procedures such as photorefractive keratotomy (PRK), phototherapeutic keratectomy (PTK), laser in situ keratomileusis (LASIK), and the like.

Laser ablation procedures can reshape or sculpt the shape of the cornea for varying purposes, such as for correcting myopia, hyperopia, astigmatism, and other corneal surface profile defects. In known systems, the laser beam often comprises a series of discrete pulses of laser light energy, with the total shape and amount of tissue being removed being determined by the position, shape, size, and/or number of a pattern of laser energy pulses impinging on the cornea. A variety of algorithms may be used to calculate the pattern of laser pulses used to reshape the cornea so as to correct a refractive error of the eye.

Accurate control of the laser beam delivery system is crucial for patient safety and successful vision correction. Accordingly, laser beam delivery systems are calibrated to ensure control over the distribution of ablation energy across the cornea so as to minimize undesirable laser system performance, such as might result from flawed internal mechanical or optical components. In particular, calibration of the laser system helps ensure accurate removal of the intended shape and quantity of the corneal tissue so as to provide the desired shape and refractive power modification to the patient's cornea. Imprecise control of the laser beam may jeopardize the success of the surgery and could cause damage to the patient's eye. For example, derivation from a desired laser beam shape, size, or position, such as the laser beam exhibiting a non-symmetrical shape or an increased or decreased laser beam diameter, may result in tissue ablation at an undesired location on the patient's cornea which in turn leads to less than ideal corneal sculpting results. As such, it is beneficial to provide precise control over the shape and size profiles as well as positioning of the laser beam so as to accurately sculpt the patient's cornea through laser ablation.

Ablation of plastic test materials are often performed prior to laser surgery to calibrate the ablation shape and size of the laser beam delivery system. For example, an iris or other variable diameter aperture which may be used to tailor the shape, size, and position of the laser beam is typically calibrated by directing laser pulses at different iris settings onto a clear plastic material. Eye loops are then used by an operator for manual inspection of the ablated plastic. Such calibration techniques are limited by many factors, such as the precision provided by the eye loops, which is typically about ±0.1 mm, and/or the vision of the operator. For example, visual measurement of shape profiles is particularly difficult and is often subject to human error. Further, such calibration techniques may not accurately measure a hysteresis of the variable diameter iris. Moreover, increased utilization of wavefront technologies to provide customized ablations in laser eye surgery systems may be optimized by increasing the accuracy of the shape, size, and positioning of the ablating laser beam.

In light of the above, it would be desirable to provide improved methods and systems for calibrating laser beam positioning, shape profile, and/or size profile with increased precision and accuracy. It would be particularly desirable if such methods and systems provided for iris calibration as well as hysteresis measurement. It would be further desirable if such methods and systems enhanced calibration accuracy without significantly increasing the overall system cost and complexity. At least some of theses objectives will be met by the methods and systems of the present invention described hereinafter.

2. Description of the Background Art

Methods, systems, and apparatus for calibrating lasers are described in U.S. Pat. Nos. 6,195,164; 6,559,934; and 6,666,855, and assigned to the assignee of the present application. PCT Publication No. WO 01/10322 describes systems, devices, and methods for verifying the positioning or adjustment of a laser beam, and is also assigned to the assignee of the present application. Further laser calibration devices and methods are described in U.S. Pat. Nos. 3,364,493; 5,078,491; 5,261,822; 5,267,012; 5,772,656; 6,116,737; 6,129,722; 6,210,169; and 6,210,401.

The full disclosures of each of the above mentioned references are incorporated herein by reference.

BRIEF SUMMARY OF THE INVENTION

The present invention provides methods and systems for calibrating a laser beam delivery system, such as an excimer laser system for selectively ablating a cornea of a patient's eye. In particular, improved methods and systems are provided for laser beam positioning, shape profile, and/or size profile calibration using an image capture device, such as a microscope camera. The methods and systems are particularly suited for iris calibration and hysteresis measurement of a variable diameter aperture. Such methods and systems further provide enhanced calibration accuracy and precision without significantly increasing the overall system cost and complexity and may be applied to a variety of laser systems.

In a first aspect of the present invention, a method for calibrating laser pulses from a laser eye surgery system using an image capture device comprises imaging an object of known size placed on a calibration surface with an image capture device. A pulsed laser beam is directed onto the calibration surface so as to leave a mark on the calibration surface, wherein the known object is removed prior to directing the pulsed laser beam onto the calibration surface. The mark on the calibration surface is then imaged with the image capture device. The laser eye surgery system is calibrated by comparing the image of the mark on the calibration surface to the image of the known object.

The imaging of the known object and of the mark on the calibration surface is carried out in the same position. Moreover, the directing and imaging may also be carried out in the same plane. For example, the directing and imaging may be carried out in at least one of a laser focus plane or an eye treatment plane, wherein imaging of the known object and imaging of the mark on the calibration surface are performed along an imaging optical path coaxial with a laser optical path. However, it will be appreciated that the directing and imaging may also be carried out in different planes. For example, the laser energy may be directed onto the calibration surface at the laser focus plane while the imaging of the known object and imaging of the mark on the calibration surface are performed at the treatment plane. In a more general system, it would be preferable to focus the laser and image capture device in the same plane.

Typically, the imaged object comprises a circular shape having a known diameter. For example, the known object may comprise a circular chrome layer on a glass or crystal plate. The calibration surface may comprise a variety of materials, including photosensitive material, silkscreen material, Zapit paper, luminescent material, or photographic material. Preferably, a photosensitive material is utilized, wherein the mark on the calibration surface comprises a permanent change in color, such as a white spot on a black background or vice versa, or a luminescent glow. Alternatively, the calibration surface may comprise photoreactive material, polymethylmethacrylate material, or other VISX calibration materials, available from VISX, Incorporated of Santa Clara, Calif. For example, use of polymethylmethacrylate material may result in the mark on the calibration surface to comprise an ablation.

The mark on the calibration surface may be associated with an iris diameter setting in a range from about 0.65 mm to about 6.7 mm. During the iris calibration procedure, the pulsed laser beam diameter setting is increased over time so as to form a plurality of marks. The resulting marks are then imaged and compared to the known object. Similarly, the pulsed laser beam diameter setting is decreased over time so as to form another set of marks that are imaged and compared to the known object. A hysteresis determination may then be determined of a variable aperture, due to changes in iris diameter setting movement directions, as well as a relationship between laser beam diameter and motor counts associated with the iris setting.

The shape of the laser beam and a center position of the laser beam may be determined from the imaging comparison. Additionally, a drift of the laser eye surgery system may be determined by monitoring a variance in center positions for each scanned and imaged laser pulse. Still further, a laser beam deflection may be determined. In some embodiments, an optical element may be rotated along a laser delivery path for smoothing laser beam integration, as discussed in greater detail in co-pending U.S. patent application Ser. No. 10/366,131, filed Feb. 12, 2003, assigned to the assignee of the present application and incorporated herein by reference. The present calibration method may also identify a rotation-induced laser induced wobble from a plurality of marks due to rotation of the optical element. Upon completion of calibration, a patient's cornea may be ablated to correct a variety of vision defects, including myopia, hyperopia, astigmatism, and other corneal surface profile defects.

In another aspect of the present invention, a method for calibrating laser pulses from a laser eye surgery system using a microscope camera is provided. The method generally comprises imaging an object of known size with a microscope camera. A pulsed laser beam is scanned across a photosensitive material so as leave an ablation on the photosensitive material. The ablation on the photosensitive material is imaged with the microscope camera. An iris calibration of a laser eye surgery system is then determined by comparing the image of the ablation on the photosensitive material to the image of the known object. Finally, a patient's cornea may be ablated with the calibrated system.

In still another aspect of the present invention, a system for calibrating laser pulses from a laser beam delivery system comprises an image capture device orientated toward a treatment plane. A known object is positionable for imaging by the image capture device. A pulsed laser beam delivery system is also provided. A calibration surface is supportable in an optical path of the pulsed laser beam so as to result in a mark on the calibration surface and for imaging of the mark on the calibration surface by the image capture device. A processor is coupled to the image capture device. The processor determines a calibration of the laser beam delivery system by comparing the image of the mark on the calibration surface to the image of the known object. The laser beam delivery system preferably comprises a laser eye surgery system. The image capture device preferably comprises a microscope camera. Optionally, video cameras, eye tracking cameras, or other existing image capture devices and cameras already provided on the laser system may be utilized.

As discussed above, the known object preferably comprises a circular chrome layer of known diameter on a glass plate. The known object and calibration surface are imaged in the same position, wherein the known object and calibration surface are positioned in at least one of a laser focus plane or the treatment plane. The calibration surface comprises photosensitive material, silkscreen material, Zapit paper, luminescent material, photoreactive material, polymethylmethacrylate material, or photographic material. The mark on the calibration surface comprises an ablation, a permanent change in color, or a luminescent glow and has an iris setting in a range from about 0.65 mm to about 6.7 mm.

A further understanding of the nature and advantages of the present invention will become apparent by reference to the remaining portions of the specification and drawings.

BRIEF DESCRIPTION OF THE DRAWINGS

The following drawings should be read with reference to the detailed description. Like numbers in different drawings refer to like elements. The drawings, which are not necessarily to scale, illustratively depict embodiments of the present invention and are not intended to limit the scope of the invention.

FIGS. 4A and 4B illustrate exploded views of images of ablated material that were ablated in a laser focus plane and imaged in an eye treatment plane.

FIGS. 5A and 5B illustrate exploded views of images of ablated material that were ablated and imaged in a laser focus plane.

FIGS. 6A and 6B illustrate exploded views of images of ablated material that were ablated and imaged in an eye treatment plane.

FIG. 7 is a table summarizing image measurements from the various ablation and imaging planes.

DETAILED DESCRIPTION OF THE INVENTION

The present invention provides methods and systems for calibrating a laser beam delivery system, such as an excimer laser system for selectively ablating a cornea of a patient's eye. In particular, improved methods and systems are provided for laser beam positioning, shape profile, size profile, drift, and/or deflection calibration using an image capture device, such as a microscope camera, for enhanced calibration accuracy and precision. The methods and systems are particularly suited for iris calibration and hysteresis measurement of a variable diameter aperture. By determining such characteristics, a desired corneal ablation treatment can be accurately effected without the laser beam becoming incident on undesired locations of corneal tissue causing off-center ablations. The calibration methods and systems of the present invention may be utilized upon replacement of any laser delivery system component, e.g., internal mechanical or optical components such as the iris, major optical re-alignment of the system, or problems with error generation.

Figure 1:
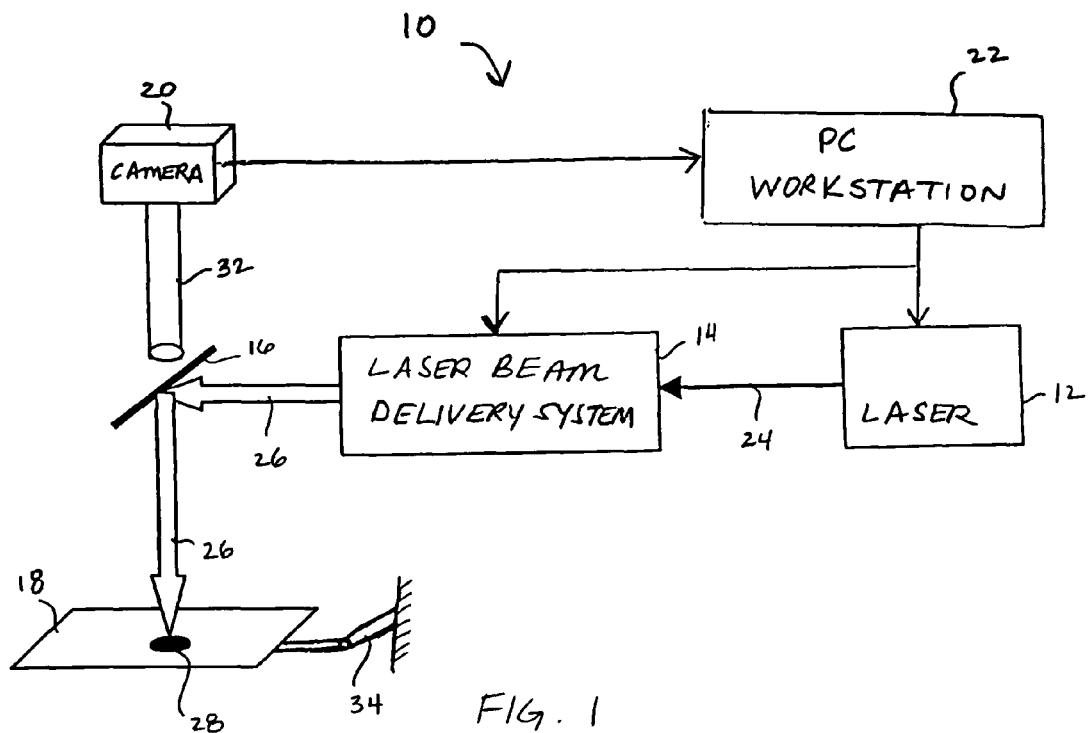
FIG. 1 illustrates a schematic of a system for calibrating laser pulses from a laser beam delivery system constructed in accordance with the principles of the present invention.

Referring now to FIG. 1, an exemplary calibration system 10 constructed in accordance with the principles of the present invention for calibrating laser pulses from a laser eye surgery system is schematically illustrated. System 10 is particularly useful for calibrating and aligning a laser ablation system of the type used to ablate a region of the cornea in a surgical procedure, such as an excimer laser used in photorefractive keratotomy (PRK), phototherapeutic keratectomy (PTK), laser in situ keratomileusis (LASIK), and the like. The system 10 generally comprises a laser 12, a laser beam delivery system 14, a surface, such as a photochromic mirror 16, a known object 30, a calibration surface 18, an image capture device 20, and a PC workstation 22. It will be appreciated that the above depictions are for illustrative purposes only and do not necessarily reflect the actual shape, size, or dimensions of the calibration system 10. This applies to all depictions hereinafter.

Figure 2:
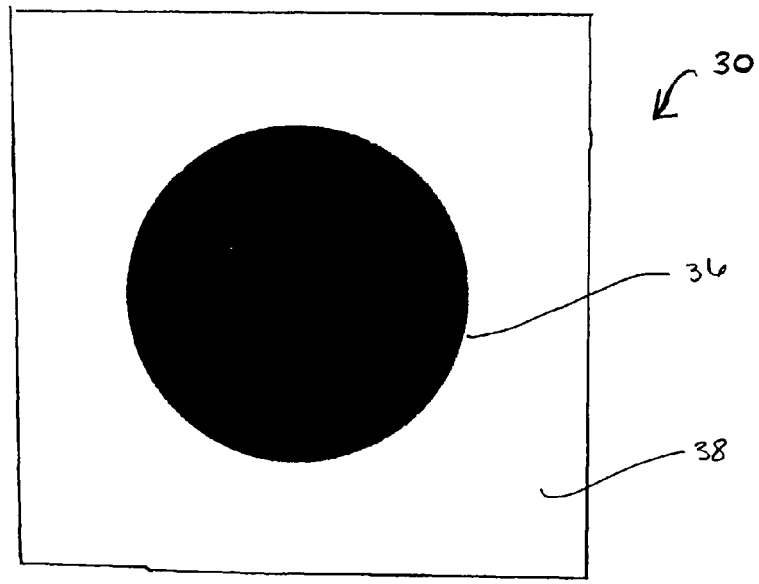
FIG. 2 illustrates an exploded view of a known object that may be employed in the system of FIG. 1.

The image capture device 20, preferably a microscope camera, is oriented toward an eye treatment plane. The known object 30, as illustrated in FIG. 2, is positioned along an imaging optical path 32 via a hinged support arm or mechanism 34 that allows movement of the known object 30 and calibration surface 18 in at least one of a laser focus plane or the treatment plane. Optionally, the known object 30 may be placed on top of a block (not shown) coupled to the arm 34. In either embodiment, the known object 30 is imaged by the microscope camera 20 and then removed. The laser 12 typically directs an unshaped laser beam 24 through the delivery system optics 14 which in turn directs a shaped and positioned laser beam 26 towards the mirror 14 having a reflecting surface that directs the laser beam 26 onto the calibration surface 18 so as to leave a mark 28 on the calibration surface 18. The mark 28 on the calibration surface 18, which is positioned along the imaging optical path 32 coaxial with the laser optical path 26, is then imaged by the microscope camera 20. A PC workstation 22 determines a calibration of the laser beam delivery system 14 by comparing the image of the mark 28 on the calibration surface 18 to the image of the known object 30. The PC workstation 22 generally includes a processor, random access memory, tangible medium for storing instructions, a display, and/or other storage media such as hard or floppy drives.

The laser 12 may include, but is not limited to, an excimer laser such as an argon-fluoride excimer laser producing laser energy with a wavelength of about 193 nm. Alternative lasers may include solid state lasers, such as frequency multiplied solid state lasers, flash-lamp and diode pumped solid state lasers, and the like. Exemplary solid state lasers include ultraviolet solid state lasers producing wavelengths of approximately 188-240 nm such as those disclosed in U.S. Pat. Nos. 5,144,630, and 5,742,626; and in Borsutzky et al., *Tunable UV Radiation at Short Wavelengths* (188-240 *nm*) *Generated by Sum-Frequency Mixing in Lithium Borate*, Appl. Phys. B 52, 380-384 (1991), the full disclosures of which are incorporated herein by reference. A variety of alternative lasers might also be used, such as infrared or femtosecond lasers. For example, a pulsed solid state laser emitting infrared light energy may be used as described in U.S. Pat. Nos. 6,090,102 and 5,782,822, the full disclosures of which are incorporated herein by reference. The laser energy generally comprises a beam formed as a series of discrete laser pulses, and the pulses may be separated into a plurality of beamlets as described in U.S. Pat. No. 6,331,177, the full disclosure of which is incorporated herein by reference.

As discussed above, the optical delivery system 14 preferably employs the ultraviolet laser beam in corneal ablation procedures to ablate corneal tissue in a photodecomposition that does not cause thermal damage to adjacent and underlying tissue. Molecules at the irradiated surface are broken into smaller volatile fragments without substantially heating the remaining substrate; the mechanism of the ablation is photochemical, i.e. the direct breaking of intermolecular bonds. The ablation removes a layer of the stroma to change its contour for various purposes, such as correcting myopia, hyperopia, and astigmatism. Such systems and methods are disclosed in the following U.S. patents, the disclosures of which are hereby incorporated by reference in their entireties for all purposes: U.S. Pat. No. 4,665,913 issued May 19, 1987 for "METHOD FOR OPHTHALMOLOGICAL SURGERY"; U.S. Pat. No. 4,669,466 issued Jun. 2, 1987 for "METHOD AND APPARATUS FOR ANALYSIS AND CORRECTION OF ABNORMAL REFRACTIVE ERRORS OF THE EYE"; U.S. Pat. No. 4,732,148 issued Mar. 22, 1988 for "METHOD FOR PERFORMING OPHTHALMIC LASER SURGERY"; U.S. Pat. No. 4,770,172 issued Sep. 13, 1988 for "METHOD OF LASER-SCULPTURE OF THE OPTICALLY USED PORTION OF THE CORNEA"; U.S. Pat. No. 4,773,414 issued Sep. 27, 1988 for "METHOD OF LASER-SCULPTURE OF THE OPTICALLY USED PORTION OF THE CORNEA"; U.S. Pat. No. 5,163,934 issued Nov. 17, 1992 for "PHOTOREFRACTIVE KERATECTOMY"; and U.S. Pat. No. 5,556,395 issued Sep. 17, 1996 for "METHOD AND SYSTEM FOR LASER TREATMENT OF REFRACTIVE ERROR USING AN OFFSET IMAGE OF A ROTATABLE MASK."

Referring now to FIG. 2, the known object 30 may comprise a circular chrome layer 36 having a 10 mm diameter on a glass plate 38. The use of the image of the known object 30 allows the magnification of the microscope camera to be quantified. A fitting routine then accurately and precisely estimates the cross-sectional shape, size, and center position of the laser beam by comparison. Matrices of such images may further be used to determine both long and short term drift of the laser eye surgery system. The known object 30 is imaged prior to directing the pulsed laser beam 26 onto the calibration surface 18 so that the mark 28 diameters may be calculated as the calibration procedure advances. In some instances, the image produced may be slightly out of focus if the known image 30 is positioned at the laser focus plane due to the fact that the camera 20 is oriented towards the treatment plane. Further, the camera 20 response itself may also be responsible for some slight elliptical distortions of the image. Hence, the image of the known object 30 is initially fit to an elliptical algorithm to account for such camera distortion. The vertical and horizontal dimensions of the chrome dot 36 are obtained and all subsequent images of the mark 28 may be rescaled according to the relative dimensions of the image of the known object 30 and fit to a circle algorithm so that the characteristics of the laser beam may be precisely obtained. It will be appreciated that the illumination level should be set to the correct level prior to capturing any images with the camera 20.

Figure 3:
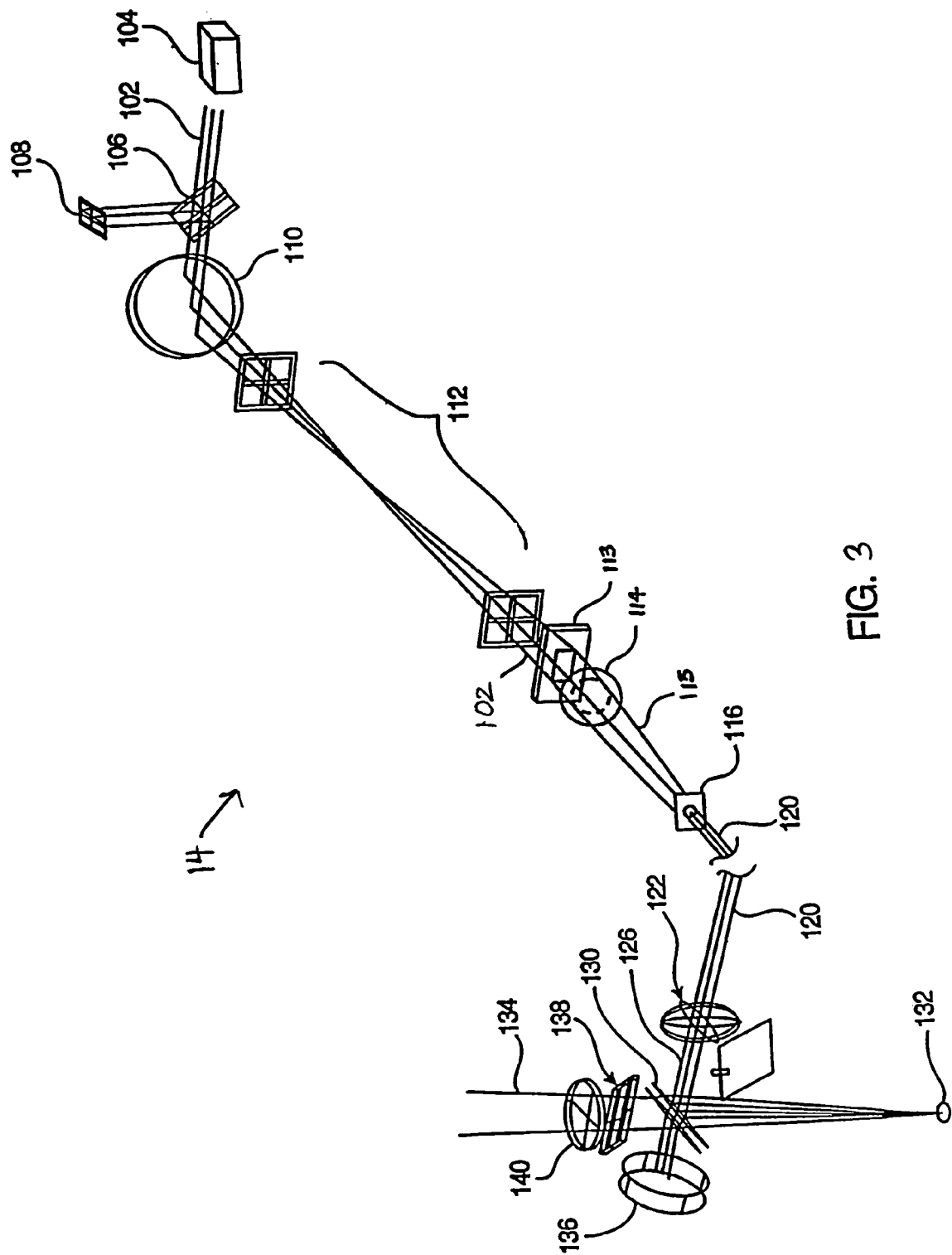
FIG. 3 illustrates a schematic view of an embodiment of the laser beam delivery system illustrated in FIG. 1.

Referring now to FIG. 3, an embodiment of the laser beam delivery system 14 of FIG. 1 is schematically illustrated. As seen in FIG. 3, a beam 102 is generated from a suitable laser source 104, such as an argon fluoride (ArF) excimer laser beam source for generating a laser beam in the far ultraviolet range with a wavelength of about 193 nm. The laser beam 102 is directed to a beam splitter 106. A portion of the beam 102 is reflected onto an energy detector 108, while the remaining portion is transmitted through the beam splitter 106. The reflective beam splitter 106 may comprise a transmitting plate of partially absorbing material to attenuate the laser beam. The transmitted laser beam 102 is reflected by an adjustable mirror 110 that is used to align the path of the laser beam. In alternate embodiments, a direction of the laser beam path may be controlled with adjustable prisms. The laser beam 102 reflects from the mirror 110 onto a rotating temporal beam integrator 112 that rotates a path of the laser beam. Another type of temporal beam integrator may be used to rotate the beam. The rotated beam emerging from the temporal integrator 112 is directed to a diffractive optic apparatus including a diffractive optic 113. In a preferred embodiment, the diffractive optic 113 is rotated with the beam 102. The diffractive optic is designed so that rotation of the diffractive optic 113 does not substantially change the path of the laser beam, and the path of the laser beam is stable with respect to rotation of the diffractive optic. The beam passes through the diffractive optic 113 and positive lens 114 and emerges as a converging beam 115.

The converging beam 115 travels to the spatial integration plane at which a variable diameter aperture 116 is disposed. The spatial integration plane is disposed near the focal point of the positive lens 114. An apertured beam 120 emerges from the variable aperture 116. The variable aperture 116 is desirably a variable diameter iris combined with a variable width slit (not shown) used to tailor the shape and size profile of the beam 115 to a particular ophthalmological surgery procedure. The apertured beam 120 is directed onto an imaging lens 122, which may be a biconvex singlet lens with a focal length of about 125 mm. The beam 126 emerging from the imaging lens 122 is reflected by a mirror/beam splitter 130 onto the surgical plane 132. The apex of the cornea of the patient is typically positioned at the surgical plane 132. Imaging lens 122 may be moved transverse to the beam to offset the imaged beam in order to scan the imaged beam about the surgical treatment plane 132. A treatment energy detector 136 senses the transmitted portion of the beam energy at the mirror/beam splitter 130. A beam splitter 138, a microscope objective lens 140, and the microscope camera 20 form part of the observation optics. The beam splitter is preferably coupled to the microscope camera 20 to assist in iris calibration as well as for viewing and recording of the surgical procedure. A heads-up display may also be inserted in the optical path 134 of the microscope objective lens 140 to provide an additional observational capability. Other ancillary components of the laser optical system 14 such as the movable mechanical components driven by an astigmatism motor and an astigmatism angle motor, have been omitted to avoid prolixity.

Referring now to FIGS. 4A and 4B, exploded views of images that were scanned in a laser focus plane and imaged in an eye treatment plane are illustrated. As noted above, the known object 30 and calibration surface 18, which are preferably imaged in the same plane, may be positioned in at least one of a laser focus plane or a treatment plane. The imaging of the chrome dot 36 and imaging of the mark 28 on the calibration surface 18 are performed along the imaging optical path 32 coaxial with the laser optical path 26. Typically, the pulsed laser beam 26 is oriented towards the laser focus plane and the camera 20 is orientated towards the treatment plane, which is a few millimeters below the laser focus plane. FIG. 4A illustrates a 1 mm image of a mark 40 and FIG. 4B illustrates a 5 mm image of a mark 42. Both images of the marks 40, 42 were created from directing the laser beam at the laser focus plane so as to create a crisp duodecahedral pattern on the calibration surface 18. The operator then moves the calibration surface 18 to a treatment plane via the calibration arm 34 or block (not shown) so that a sharp image of the marks 40, 42 may be obtained for calibration purposes. The calibration surface 18 preferably comprises silkscreen or luminescent material, wherein the marks 40, 42 comprise a permanent change in color or a luminescent glow. For example, the luminescent material may comprise a piece of glass, crystal, or polymer that is optically activated, such as chromium doped, and has a relatively long luminescent lifetime. Images may be recorded after each laser pulse, wherein the luminescence of the mark will have decayed before the next laser pulse is directed onto the luminescent surface.

FIGS. 5A and 5B illustrate exploded views of images that were scanned and imaged in the same plane, namely the laser focus plane. FIG. 5A illustrates a 1 mm image of a mark 40' and FIG. 5B illustrates a 5 mm image of a mark 42'. Both images of the marks 40, 42 were created from directing the laser beam at the laser focus plane so as to create a crisp duodecahedral pattern on the calibration surface 18. The image of the marks 40', 42' however are also taken at the laser focus plane. The images produced 40', 42' may be slightly out of focus as the camera 20 is oriented towards the treatment plane, a few millimeters below the laser focus plane. However, such deviations are minor as discussed in more detail below with reference to FIG. 7. Further, directing and imaging in the laser focus plane can be automatically implemented without operator intervention. FIGS. 6A and 6B illustrate exploded views of images that were scanned and imaged in the eye treatment plane. FIG. 5A illustrates a 1 mm image of a mark 40" and FIG. 5B illustrates a 5 mm images of a mark 42". Although this image capture positioning involves minimal operator intervention as well, it can be seen that the defocus of the laser may result in varying gray zones, poor contrast, and other variations in the images 40", 42", which are not apparent when the laser beam is scanned in the laser focus plane.

Referring now to FIG. 7, a table summarizing image measurements from the scanning and imaging positions of FIGS. 4A, 4B, 5A, and 5B as well as measurement results obtained from utilizing a Tencor Profilometer are shown. The first column indicates measurements made with the iris 116 set at various diameter settings from about 0.65 mm to about 6.0 mm. The profilometer measurements, which served as the reference measurements, were taken for each iris setting as indicated in the second column. The third column represents image measurements that were scanned in the laser focus plane and imaged in the treatment plane, as depicted by FIGS. 4A and 4B. The fourth column represents measurements that were scanned and imaged in the laser focus, as depicted by FIGS. 5A and 5B. The fifth column represents any measurement variations between the third and fourth columns. The sixth column represents any measurement variations between the second and third columns. The best possible accuracy of the fit is taken to be of the order of 1 pixel, which is about 0.02 mm. In general, Table 7 shows that utilizing either an up/down fit (FIGS. 4A, 4B) or an up/up fit (FIGS. 5A, 5B) provides a relatively accurate and precise image measurement. The small differences between measured images, as indicated in the fifth and sixth columns, are largely smaller than or of the order of the pixel resolution. Moreover, improved image contrast, such as by choosing a higher quality silkscreen or other calibration surfaces, may further minimize any variations in measurement readings.

Figure 8A:
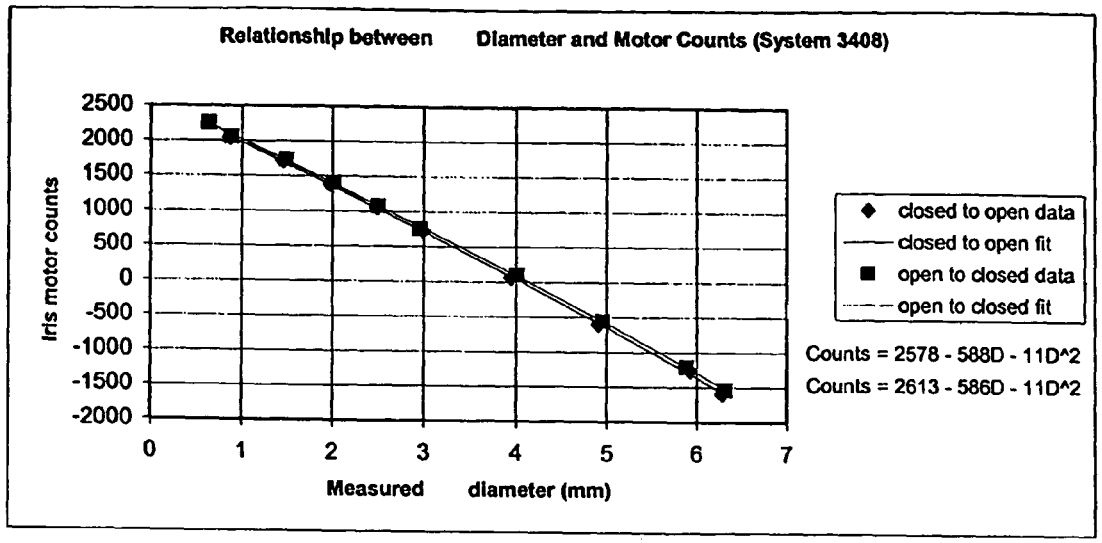
FIGS. 8A through 8B are graphical representations illustrating the relationship between laser beam diameter and motor counts associated with an iris setting.
Figure 8B:
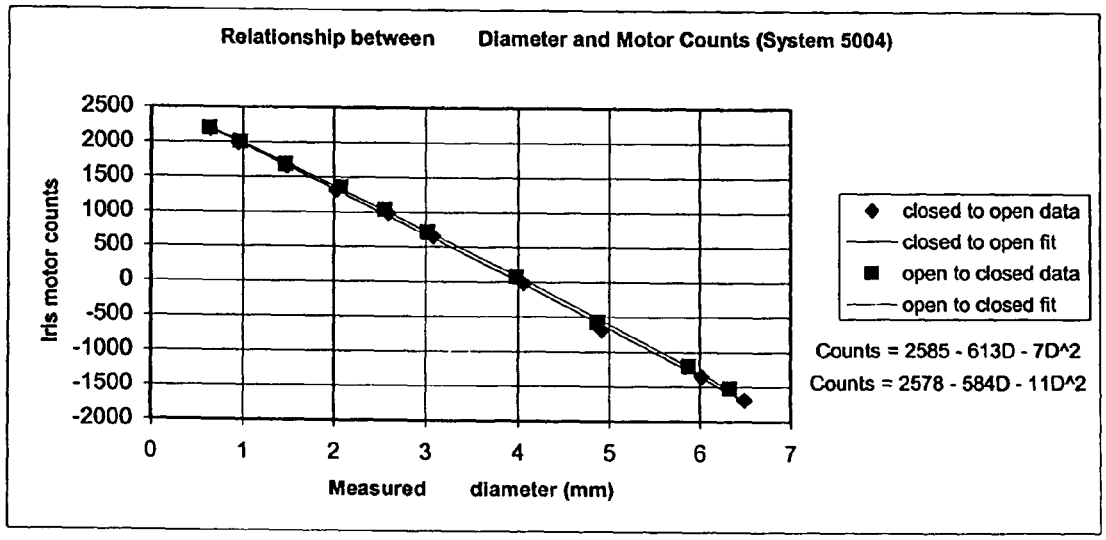

Referring now to FIGS. 8A and 8B, graphs illustrating the relationship between laser beam diameter and motor counts associated with the iris setting are depicted. In particular, a total of twenty laser mark images are obtained, in two data sets of ten. The first ten are carried out by increasing the laser beam diameter setting of the iris 116 over time from 0.7 mm, 1.0 mm, 1.5 mm, 2.0 mm, 2.5 mm, 3 mm, 4 mm, 5 mm, 6 mm, and 6.5 mm. Each mark or ablation is produced by firing 100 pulses at 20 Hz with energy between 180-220 mJ from the laser 12 onto the calibration surface 18. A one second pause allows any smoke to dissipate prior to capturing the image of the mark 28 with the camera 20 and calculating the measured iris diameter by comparison to the known object 30. The next 100 pulses are then fired at the next increasing diameter without moving the calibration surface 18. This routine will continue through the 6.5 mm setting and will take about one minute. The second set of marks or ablations 28 will proceed in a similar manner except that a new calibration surface or a different place on the existing calibration surface will be utilized and the iris 116 will be cycled to the 6.7 mm diameter setting wherein the pulsed laser beam diameter setting is decreased over time. In general, the scanning and imaging process is time efficient in that it generally takes less than three minutes to complete. By comparing both data sets, any hysteresis due to changes in iris diameter setting movement directions may be determined for the iris 116 and accounted for. Moreover, both sets of data may be used to produce interpolation curves for determining an accurate relationship between measured laser beam diameter and motor counts associated with an iris aperture.

Figure 8C:
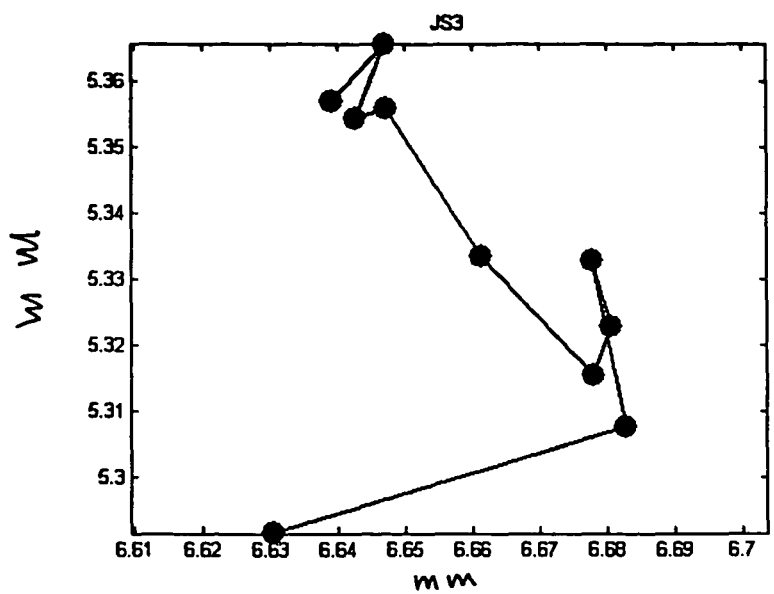
FIGS. 8C through 8D are graphical representations illustrating the hysteresis relationship.
Figure 8D:
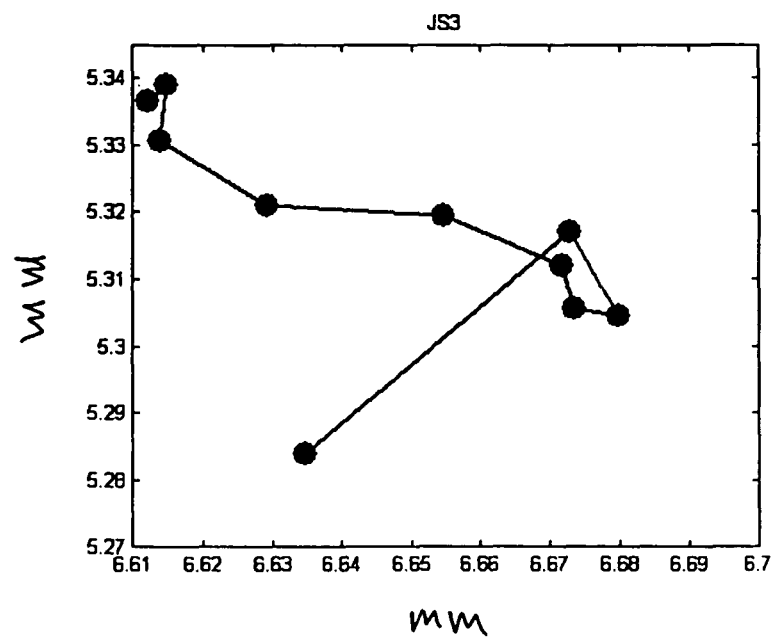

Typical results are shown in FIGS. 8A and 8B for two different laser systems. The data obtained from the calibration procedure is fit into two quadratic lines, one for increasing laser beam diameter setting (closed to open) and one for decreasing laser beam diameter setting (open to closed). As can be seen, both irises 116 have similar characteristics. There is evidence that there is a small amount of hysteresis, justifying that dual curves should be retained. The best fit quadratic expressions suggest that there is a small amount of non-linearity that should to taken into consideration. As such, the best fit for determining a relationship between laser beam diameter and motor counts associated with the iris is a quadratic fit, rather than a linear fit relationship, for iris calibration purposes. Any desired laser beam shape and position can thereafter be produced through the use of such relationships obtained during the calibration procedure. FIGS. 8C and 8D further illustrate iris measurements from "closed to open" and "open to closed" respectively to capture the hysteresis of the iris. The dots represent center.

A drift of the laser eye surgery system 14 may be determined by monitoring a variance in center positions for each scanned and imaged laser pulse. It will be appreciated that drifts may be dependent upon several factors, such as the manner in which the laser is used between measurements, the particular set of system parameters, and/or changes in environmental conditions such as temperature. Still further, a laser beam deflection may be determined. As the iris 116 changes diameter, the center of the aperture may shift slightly. As a result of the calculations already performed, the center of the best fit to the shape of the dodecagon pattern on the calibration surface has been determined for each iris size. A plot of the x and y positions of the shape center can then be computed as a function of iris diameter. Best fit lines can be independently fit through the x and y positions as a function of iris diameters. Hence, when a particular diameter is required by a treatment the necessary correction for the shift of the laser beam can be calculated from these lines and the laser beam target position adjusted accordingly.

The techniques of the present invention can also be applied to judge the stability of the laser delivery system 14. The calibration arm 34 supporting the calibration surface 18 may comprise a luminescent plate. After each laser pulse, an image is captured while the plate is still emitting light. Images are then analyzed as described above. The center positions are calculated and may be plotted on x and y axes so that the plot provides a map of where the laser pulses landed. This plot can then be used to determine any systematic movement of the laser beam with time. Alternatively, the raw data can be used to determine parameters such as the statistical variations in x and y positions.

Referring back to FIG. 3, a number of the optical elements in the optical system 14 may be rotated along the laser delivery path, as described in detail in co-pending U.S. patent application Ser. No. 10/366,131, to distribute any distortion caused by imperfections of the optical elements. In a preferred embodiment, the lens 114 is rotated around its axis. In other embodiments, the beam splitter 106 may be moved along its plane; the mirror 110 may be moved along its plane; the diffractive optic 113 may be moved in its plane, and the mirror/beam splitter 130 may be moved along its plane. Although the path of the light beam is stable with respect to movement of an optical element, minor deviations in the position of the optical center about the axis of rotation may occur, and such deviations may induce a slight wobble in the path of the laser beam as the optical element rotates. Advantageously, the present invention may also be utilized to identify a rotation-induced laser induced wobble from a plurality of marks. Analysis of images of the marks may help account for these small deviations due to rotation of the optical element.

Figure 9A:
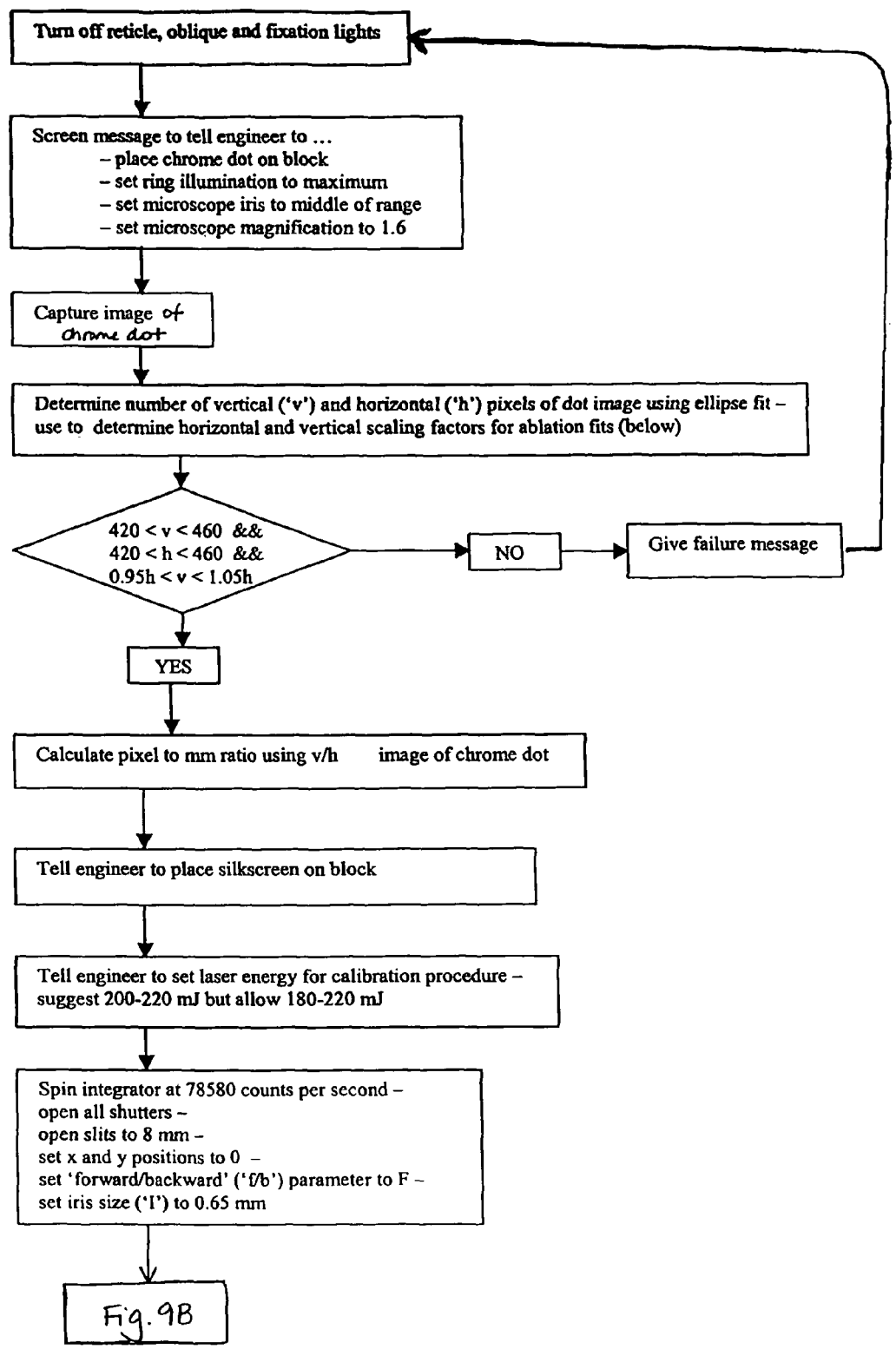
FIGS. 9A and 9B are simplified flow charts illustrating a method for calibrating laser pulses employing the system of FIG. 1.
Figure 9B:
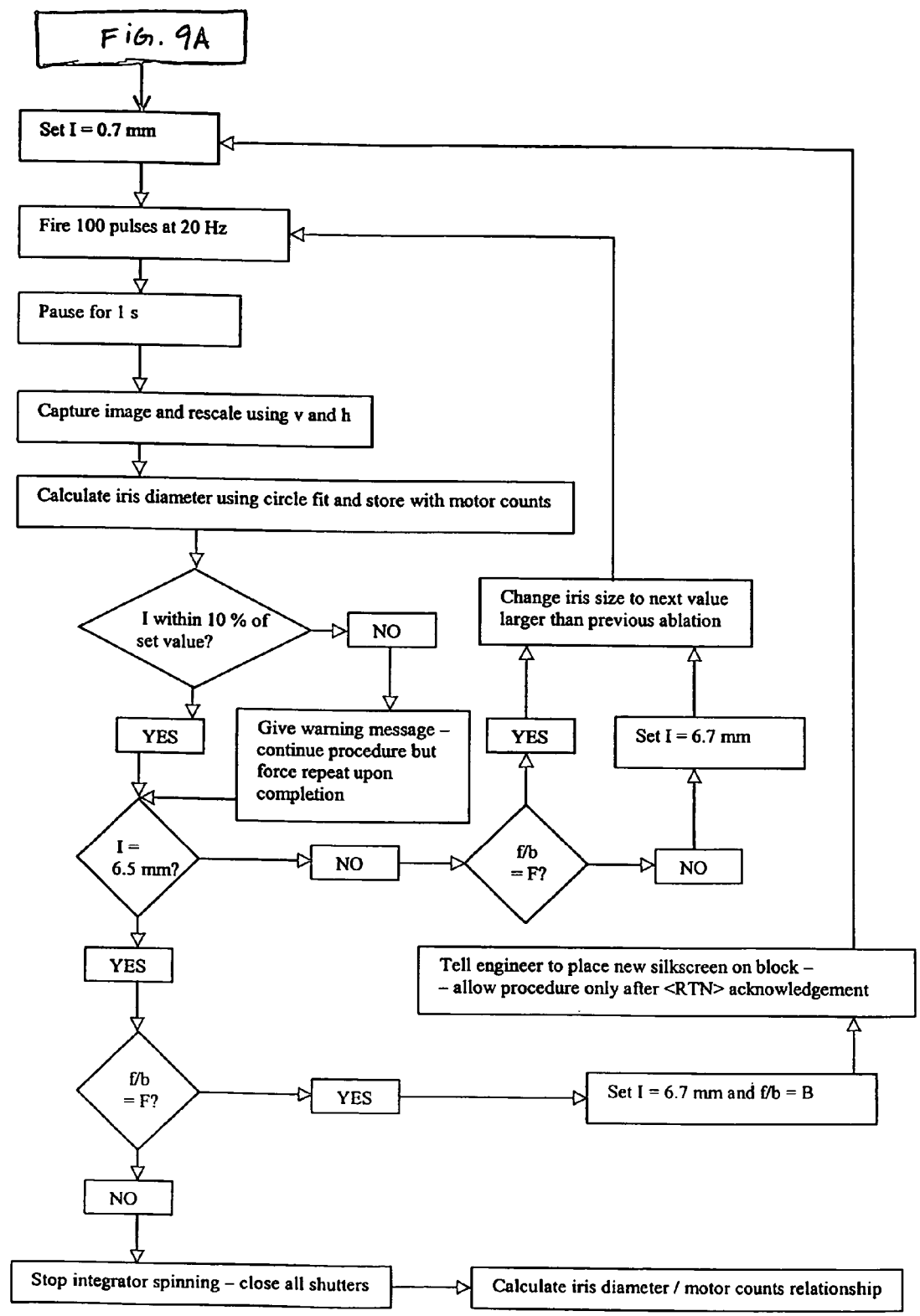

Referring now to FIGS. 9A and 9B, simplified flowcharts illustrate a method for calibrating laser pulses employing the system of FIG. 1. As shown in FIG. 9A, the operator will begin by adjusting the illumination of the microscope camera 20 by turning the ring illumination setting to maximum and all other illuminations settings (e.g., reticle, oblique, and fixation lights) off. The chrome dot 36 is placed on a block coupled to the calibration arm 34. The microscope iris and magnification are also set. The image of the chrome dot 36 is then captured and the number of vertical and horizontal pixels of the dot image 36 calculated using an elliptical algorithm. The acceptable range for pixels in both directions is 420-460 and the values should be within 5% of each other. If this tolerance is not met, a failure message is indicated on the screen indicating that the image of the chrome dot 36 is out of range, not placed flat, or that the camera is misaligned and to start the procedure again. If the pixel tolerance is met, the pixel to mm ratio is determined using the vertical to horizontal pixel ratio of the dot image 36. The operator than replaces a calibration plastic 18, such as a silkscreen, for the chrome dot 36 and sets the laser energy for the calibration procedure between 180-220 mJ, preferably to 200-220 mJ, the spin integrator at 78580 counts, and the iris setting to 0.65 mm. All shutters and slits are open, the x and y positions are set to 0, and the forward/backward parameter is set to F.

As shown in FIG. 9B, the iris setting is changed to 0.7 mm so that the iris is being opened (increasing laser beam diameter setting). Each mark or ablation is produced by firing 100 pulses at 20 Hz with a one second pause to allow any smoke to dissipate prior to capturing the image of the mark 28 with the camera 20. The capture image is rescaled according to the relative dimensions of the image of the known object 30 and fit to a circle algorithm so that the diameter of the laser beam may be precisely obtained. If the measured value is within 10% of the set/expected value, the iris size is changed to the next value larger than the previous ablation, and the above noted procedure repeated until the iris setting of 6.5 mm is reached. If the measured value is not within 10% of the set value, a warning message is indicated on the screen that there is an error in the ablation image measurement. The procedure may be continued, but should be repeated upon completion. After reaching the iris setting of 6.5 mm, the same procedure is similarly repeated for decreasing laser beam diameter settings, wherein the iris setting is set to 6.7 mm so that the iris is being closed. The operator also receives a message on the screen to replace the calibration surface or to move it prior to imaging in the decreasing diameter setting mode. Optionally, an acknowledgment by the operator may be required to ensure that a new silkscreen has been placed on the block. Upon completion, the integrator spinning will be stopped and the shutter closed. The relationship between laser beam diameter and motor counts associating the iris setting may then be determined from these two data sets, as previously discussed with reference to FIGS. 8A and 8B.

It will be appreciated that the calibration system 10 of the present invention may be applied to different laser systems, including scanning lasers and large area laser ablation systems. Examples include the VISX STAR, STAR S2, STAR S3, STAR S4 Excimer Laser Systems, and laser systems employing wavefront technologies, all of which are commercially available from VISX, Incorporated of Santa Clara, Calif. Other laser systems include those available from Alcon Summit, Bausch & Lomb, LaserSight, Zeiss Meditec, Schwind, Wavelight Technologies, and the like.

Although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the invention. Therefore, the above description should not be taken as limiting the scope of the invention which is defined by the appended claims.

What is claimed is:

1. A method for calibrating laser pulses from a laser eye surgery system, the laser eye surgery system having an image capture device oriented for imaging an eye during laser eye surgery of the eye, the method comprising:
    imaging a known object with the image capture device of the laser eye surgery system, the imaged object having an imaged object size, an imaged object shape, and an imaged object location;
    directing a pulsed laser beam of the laser eye surgery system onto a calibration surface so as to leave a mark on the calibration surface;
    imaging the mark on the calibration surface with the image capture device of the laser eye surgery system, the imaged mark having an imaged mark size, an imaged mark shape, and an imaged mark location; and
    calibrating a laser beam cross-sectional shape, a laser beam cross-sectional location, and/or a laser beam cross-sectional size of the laser eye surgery system by comparing the image of the mark on the calibration surface to the image of the known object.

2. The method of claim 1, wherein the imaged object comprises a circular shape having a known diameter.

3. The method of claim 2, wherein the known object comprises a circular chrome layer on a glass plate.

4. The method of claim 1, further comprising removing the known object prior to directing the pulsed laser beam onto the calibration surface.

5. The method of claim 1, wherein the imaging of the known object and of the mark on the calibration surface is carried out in the same position.

6. The method of claim 1, wherein the directing and imaging are carried out in the same plane.

7. The method of claim 1, wherein the directing and imaging are carried out in at least one of a laser focus plane or a treatment plane, and wherein imaging of the known object and imaging of the mark on the calibration surface are performed along an imaging optical path coaxial with a laser optical path.

8. The method of claim 1, wherein the calibration surface comprises photosensitive material, silkscreen material, luminescent material, or photographic material.

9. The method of claim 8, wherein the mark on the calibration surface comprises a permanent change in color or a luminescent glow.

10. The method of claim 1, wherein the calibration surface comprises photoreactive material or polymethylmethacrylate material.

11. The method of claim 10, wherein the mark on the calibration surface comprises an ablation.

12. The method of claim 1, wherein the mark on the calibration surface has a diameter setting in a range from about 0.65 mm to about 6.7 mm.

13. The method of claim 1, further comprising increasing the pulsed laser beam diameter setting over time so as to form a plurality of marks, imaging the marks, and comparing the marks to the known object.

14. The method of claim 13, further comprising decreasing the pulsed laser beam diameter setting over time.

15. A method for calibrating laser pulses from a laser eye surgery system using an image capture device, the method comprising:
    imaging a known object with an image capture device;
    directing a pulsed laser beam onto a calibration surface so as to leave a mark on the calibration surface;
    imaging the mark on the calibration surface with the image capture device;
    increasing the pulsed laser beam diameter setting over time with a variable aperture so as to form a plurality of marks, imaging the marks, and comparing the marks to the known object;
    decreasing the pulsed laser beam diameter setting over time with the variable aperture; and
    calibrating the laser eye surgery system by comparing the image of the mark on the calibration surface to the image of the known object, the calibrating of the laser eye surgery system comprising determining a hysteresis of the variable aperture.

16. The method of claim 1, further comprising determining a relationship between laser beam diameter and motor counts associated with an iris setting of the laser eye surgery system by comparing the imaged object size with the imaged mark size.

17. The method of claim 1, further comprising determining a shape of the laser beam by comparing the imaged object shape with the imaged mark shape.

18. The method of claim 1, further comprising determining a center position of the laser beam by comparing the imaged object location with the imaged mark location.

19. The method of claim 1, further comprising determining a drift of the laser eye surgery system by monitoring a variance in center positions for each scanned and imaged laser pulse.

20. The method of claim 1, further comprising determining a laser beam deflection.

21. The method of the claim 1, further comprising rotating an optical element along a laser delivery path and identifying a rotation-induced laser induced wobble from a plurality of marks.

22. The method of claim 1, further comprising ablating a patient's cornea with the calibrated system.

23. A method for calibrating laser pulses from a laser eye surgery system having a microscope camera, the method comprising:

imaging a known object with the microscope camera oriented toward an eye treatment plane of the laser eye surgery system, the imaged known object having a known object size;

scanning a pulsed laser beam across a photosensitive material disposed along the eye treatment plane so as leave an ablation on the photosensitive material;

imaging the ablation on the photosensitive material with the microscope camera while the photosensitive material is disposed along the eye treatment plane, the imaged ablation having an ablation size;

determining an iris calibration of the laser eye surgery system by comparing the ablation size in the image of the ablation on the photosensitive material to the known object size in the image of the known object; and ablating a patient's cornea with the calibrated system.

* * * * *